United States Patent [19]
Burton et al.

[11] Patent Number: 5,635,501
[45] Date of Patent: Jun. 3, 1997

[54] ALPHALOSPORINS AND 1-CARBA-1-DETHIA CEPHALOSPORINS

[75] Inventors: George Burton, Wallington; John H. Bateson, Reigate; Richard L. Elliott, Banstead; Stephen C. M. Fell, Horsham, all of England

[73] Assignee: Pfizer Inc., New York, N.Y.

[21] Appl. No.: 360,763

[22] PCT Filed: Jun. 21, 1993

[86] PCT No.: PCT/GB93/01310

§ 371 Date: Jan. 25, 1995

§ 102(e) Date: Jan. 25, 1995

[87] PCT Pub. No.: WO94/00457

PCT Pub. Date: Jan. 6, 1994

[30] Foreign Application Priority Data

Jun. 26, 1992 [GB] United Kingdom ............ 9213567

[51] Int. Cl.$^6$ ............ C07D 501/48; A61K 31/545
[52] U.S. Cl. ............ 514/204; 540/226; 540/227; 514/206
[58] Field of Search ............ 540/222, 226, 540/227; 514/204, 206

[56] References Cited

U.S. PATENT DOCUMENTS 5,246,926  9/1993  Bateson et al. ............ 540/222

FOREIGN PATENT DOCUMENTS

| 0 477 717 A2 | 1/1992 | European Pat. Off. . |
| 0477717 | 1/1992 | European Pat. Off. . |
| 92/01695 | 2/1992 | WIPO . |
| WO 92/01695 | 4/1992 | WIPO . |
| WO 92/01696 | 6/1992 | WIPO . |
| WO 93/11131 | 10/1993 | WIPO . |

OTHER PUBLICATIONS

J. of Antibiotics, vol. 45, No. 12, pp. 1929–1938 Dec. 1992, Koyama et al.

*Primary Examiner*—John M. Ford
*Attorney, Agent, or Firm*—Peter C. Richardson; Gezina Holtrust; B. Timothy Creagan

[57] ABSTRACT

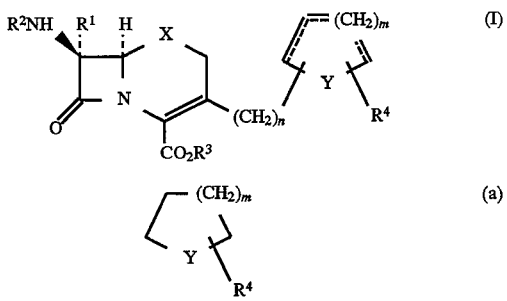

Compound of formula (I) or salts thereof wherein $R^1$ is hydrogen, methoxy or formamido; $R^2$ is an acyl group; $CO_2R^3$ is a carboxy group or a carboxylate anion, or $R^3$ is a readily removable carboxy protecting group or a pharmaceutically acceptable salt-forming group or in vivo hydrolysable ester group; $R^4$ represents hydrogen or up to four substituents; X is S, SO, $SO_2$ or $CH_2$; Y is O, S, SO or $SO_2$; n is 0 or 1; m is 1 or 2; and wherein in the (a) ring system the dotted line indicates that one pair of adjacent ring carbon atoms is joined by a C=C double bond. These compounds have antibacterial activity.

6 Claims, No Drawings

ALPHALOSPORINS AND 1-CARBA-1-DETHIA CEPHALOSPORINS

This application is a 371 of PCT/GB93/01310, filed 21 Jun. 1993.

This invention relates to novel β-lactam compounds, their preparation and their use, and in particular to a novel class of cephalosporins. These compounds have antibacterial properties, and are therefore of use in the treatment of bacterial infections in humans and animals caused by a wide range of organisms.

WO 92/01696 (Beecham Group plc) discloses cephems of general formula (A):

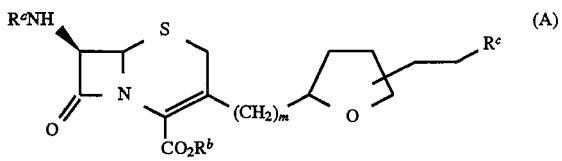

wherein $R^a$, $R^b$ and $R^c$ are various substituents and m is 0 or 1. EP 0477717A (Bayer) discloses an analagous class of compounds having a furyl ring in place of the tetrahydrofuranyl ring shown in formula (A).

We have found a particularly advantageous class of cephems and carbacephems bearing a cyclic ether or thio-ether substituent at the 3-position of the cephem nucleus.

The present invention provides a compound of formula (I) or a salt thereof:

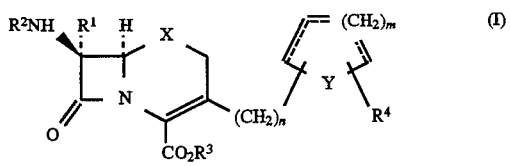

wherein:

$R^1$ is hydrogen, methoxy or formamido;

$R^2$ is an acyl group, in particular that of an antibacterially active cephalosporin;

$CO_2R^3$ is a carboxy group or a carboxylate anion, or $R^3$ is a readily removable carboxy protecting group or a pharmaceutically acceptable salt-forming group or in vivo hydrolysable ester group;

$R^4$ represents hydrogen or up to four substituents, which may be present on any of the carbon atoms in the ring system shown, selected from alkyl, alkenyl, alkynyl, alkoxy, hydroxy, halogen, amino, alkylamino, acylamino, dialkylamino, $CO_2R$, $OCOR$, $CONR_2$, $SO_2NR_2$ where R is hydrogen or alkyl, aryl and heterocyclyl, which may be the same or different and wherein any $R^4$ alkyl substituent is optionally substituted by one or more substituents selected from the list from which $R^4$ is selected;

X is S, SO, $SO_2$ or $CH_2$; Y is O, S, SO or $SO_2$; n is 0 or 1; m is 1 or 2; and wherein in the

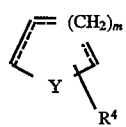

ring system the dotted line indicates that one pair of adjacent ring carbon atoms is joined by a C=C double bond.

The bonding carbon atom of the unsaturated cyclic ether or thio-ether moiety which links the ring to the cephalosporin nucleus is generally asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

Since the compounds of the present invention are intended for use as therapeutic agents for antibacterial use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

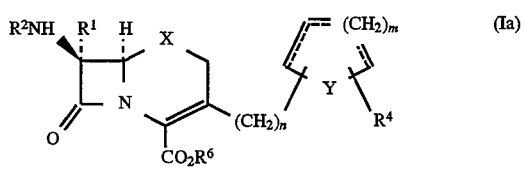

wherein $R^1$, $R^2$, $R^4$, m, n, Y, and y are as defined with respect to formula (I) and the group $CO_2R^6$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective amount of an antibiotic compound of the formula (Ia) or a pharmaceutically acceptable in vive hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

Also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group, an oxime radical of formula $-N=CHR^7$ where $R^7$ is aryl or heterocyclic, or an in vivo hydrolysable ester radical such as defined below.

A carboxyl group may be regenerated from any of the above esters by usual methods appropriate to the particular $R^3$ group, for example, acid- and base- catalysed hydrolysis, or by enzymically-catalysed hydrolysis, or by hydrogenolysis under conditions wherein the remainder of the molecule is substantially unaffected.

When used herein the term 'aryl' includes phenyl and naphthyl, each optionally substituted with up to five, preferably up to three, groups selected from halogen, mercapto, $(C_{1-6})$ alkyl, phenyl, $(C_{1-6})$ alkoxy, hydroxy$(C_{1-6})$alkyl, mercapto$(C_{1-6})$alkyl, halo$(C_{1-6})$ alkyl, hydroxy, amino, nitro, carboxy, $(C_{1-6})$alkylcarbonyloxy, $(C_{1-6})$alkoxycarbonyl, formyl, or $(C_{1-6})$alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$ alkoxy, halo$(C_{1-6})$alkyl, hydroxy, carboxy, carboxy salts, carboxy esters such as $(C_{1-6})$alkoxycarbonyl, $(C_{1-6})$ alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

The term 'heteroaryl' as used herein means a heteroaromatic heterocyclic ring or ring system, suitably having 5 or 6 ring atoms in each ring.

When used herein the terms 'alkyl', 'alkenyl', 'alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

Examples of suitable pharmaceutically acceptable in vivo hydrolysable ester groups which $R^3$ may comprise include those which break down readily in the human body to leave the parent add or its salt. Suitable ester groups of this type include those of part formulae (i), (ii), (iii), (iv) and (v):

$$-CO_2CH-O.CO.R^b \quad\quad (i)$$
$$\phantom{-CO_2CH}|\phantom{-O.CO.R^b}$$
$$\phantom{-CO_2CH}R^a$$

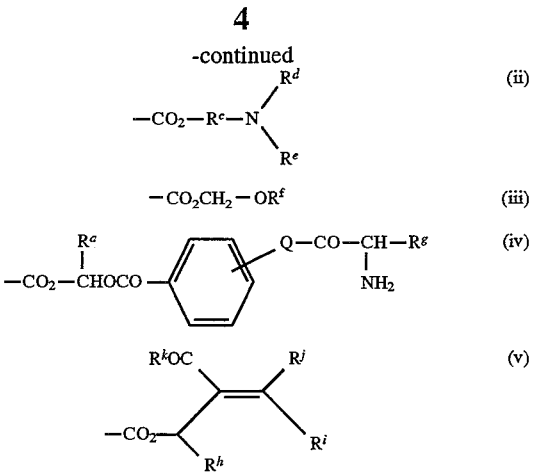

(ii), (iii), (iv), (v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$((C_{1-6})$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or hetero aryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$((C_{1-6}))$alkoxy or aryl.

Examples of suitable in vivo hydrolysable ester groups include, for example, acyloxyalkyl groups such as acetoxymethyl, pivaloyloxymethyl, α-acetexyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-lower alkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

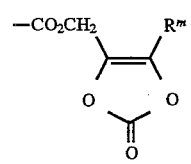

wherein $R^m$ is hydrogen, $(C_{1-6})$ alkyl or phenyl.

A preferred in vivo hydrolysable ester group is the pivaloyloxymethyl group.

Suitable pharmaceutically acceptable salts of the carboxy group of the compound of formula (I) include metal salts, e.g. alumininm, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)-amine, cycloalkylamines such as dicyclohexylamine, or with procaine, dibenzylamine, N, N-dibenzylethylene-diamine, 1-ephenamine, N-methylmorpholine, N-ethylpiperidine, N-benzyl-β-phenethylamine, dehydroabietylamine, N, N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts of formula (I) may be prepared by salt exchange in conventional manner.

In compounds of formula (I) or (Ia), the group Y may be an oxidised sulphur atom, i.e. a sulphoxide (SO) or sulphone ($SO_2$) group. When Y is a sulphoxide group it will be understood that α- and β-isomers may exist; both such isomers are encompassed within the scope of the present invention.

Preferably X is S or $CH_2$. Preferably Y is O or S, particularly O. Advantageously, $R^1$ is hydrogen.

Suitably the unsaturated cyclic ether at the 3-position of the cephalosporin nucleus is a 4,5-dihydrofuran-2-yl, a 2,3-dihydrofuran-2-yl, a 2,5-dihydrofuran-2-yl or a 3,4-dihydro-2H-pyran-6-yl group.

Suitably, the unsaturated cyclic ether or thio-ether at the 3-position of the cephalosporin nucleus is unsubstituted or substituted by up to three substituents $R^4$, selected from $(C_{1-6})$ alkyl, for example methyl, $(C_{1-6})$ alkoxy, for example methoxy, $(C_{1-6})$ alkoxycarbonyl for example methoxycarbonyl, $(C_{1-6})$ alkoxy $(C_{1-6})$ alkyl, for example methoxymethyl, and $(C_{1-6})$ alkanoyloxy $(C_{1-6})$ alkyl, for example acetoxymethyl. Preferably the cyclic ether or thio-ether at the 3-position of the cephalosporin nucleus is unsubstituted.

Preferably m is 1. Preferably n is 0.

Preferably the unsaturated cyclic ether or thio ether is bonded to the cephalosporin nucleus at a ring carbon adjacent to the oxygen or sulphur heteroatom.

Suitable acyl groups $R^2$ include those of formulae (a)–(f):

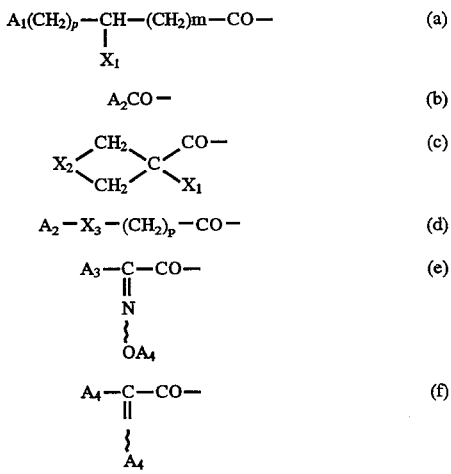

wherein p is 0, 1 or 2; m is 0, 1 or 2; $A_1$ is $(C_{1-6})$ alkyl, substituted $(C_{1-6})$ alkyl wherein the substituents may be as for $R^4$ above, $(C_{3-6})$ cycloalkyl, cyclohexenyl, cyclohexadienyl, an aryl (including heteroaryl) group, such as phenyl, substituted phenyl, thienyl, pyridyl, or an optionally substituted thiazolyl group, a $(C_{1-6})$ akylthio group or $(C_{1-6})$ alkyloxy; $X_1$ is a hydrogen or halogen atom, a carboxylic add, carboxylic ester, sulphonic acid, azido, tetrazolyl, hydroxy, acyloxy, amino, ureido, acylamino, heterocyclylamino, guanidino or acylureido group; $A_2$ is an aryl group, for example a phenyl, 2,6-dimethoxyphenyl, 2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —$CH_2OCH_2$—, —$CH_2SCH_2$— or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $(C_{1-6})$alkyl, $(C_{3-8})$ cycloalkyl, $(C_{3-8})$ cycloalkyl$(C_{1-6})$alkyl, $(C_{1-6})$ alkoxycarbonyl$(C_{1-6})$ alkyl, $(C_{2-6})$ alkenyl, carboxy$(C_{1-6})$alkyl, $(C_{2-6})$ alkynyl, aryl or $(C_{1-6})$alkyl substituted by up to three aryl groups.

Suitably when $R^2$ is a group (a), $A_1$ is $(C_{1-6})$ alkyl, $(C_{3-6})$ cycloalkyl, cyclohexenyl, cyclohexadienyl, phenyl, substituted phenyl (e.g. substituted as for "aryl" above) such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is 0.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino-1,2,4-thiadiazol-3-yl and 4-aminopyrimid-2-yl.

In compounds of formula (Ia) a preferred acyl group $R^2$ is one of formula (e), having a group, $A_3$ which is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

It will be appreciated that the 5- or 6- membered ring of the unsaturated cyclic ether or thio ether group at the 3-position of the cephalosporin system may exist in a number of isomeric forms. All isomeric forms, including mixtures of isomeric forms, are included within the scope of this invention.

Certain compounds of the invention include an amino group which may be protected. Suitable amino protecting groups are those well known in the art which may be removed under conventional conditions without disruption of the remainder of the molecule.

Examples of amino protecting groups include ($C_{1-6}$) alkanoyl; benzoyl; benzyl optionally substituted in the phenyl ring by one or two substituents selected from ($C_{1-4}$) alkyl, ($C_{1-4}$) alkoxy, trifluoromethyl, halogen, or nitro; ($C_{1-4}$) alkoxycarbonyl; benzyloxycarbonyl or trityl (ie triphenyl methyl) substituted as for benzyl above; allyloxycarbonyl, trichloro ethoxycarbonyl or chloroacetyl.

Some of the compounds of this invention may be crystallised or recrystallised from solvents such as organic solvents. In such cases solyates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following pharmaceutically acceptable carboxylic acids, and salts and in vivo hydrolysable esters thereof:

(6R,7R)-3-(5,6-dihydro-4H-pyran-2-yl)-7-phenylacetamido-ceph-3-em-4-carboxylic acid.

(6R,7R)-3-[(5,6-dihydro-4H-pyran-2-yl)methyl]-7-phenyl-acetamido-ceph-3-em-4-carboxylic acid.

(6R,7R)-3-(4,5-dihydrofuran-2-yl)-7-phenylacetamido-ceph-3-em-4-carboxylic acid.

(6R,7R)-3-(4,5-dihydrofuran-2-yl)-7-phenylacetamido-ceph-3-em-4-carboxylic acid.

(6R,7S)-7-[2-( 2-aminothiazol-4-yl )-2-(Z)-methoxylminoacetamido]-3-[(R and S)-2,5-dihydrofuran-2-yl]-1-carba-1-dethiaceph-3-em-4-carboxylic acid.

(6R,7S)-3-[(RS)-2,3-dihydrofuran-2-yl]-7-phenyl-acetamido-1-carba-1-dethiaceph-3-em-4-carboxylic acid.

(6R,7S)-3-[(RS)-2,3-dihydrofuran-2-yl]-7-phenyl-acetamido-1-carba-1-dethiaceph-3-em-4-carboxylic acid.

The present invention provides a process for the preparation of a compound of formula (I) or (Ia) as defined above in which —$CO_2R^3$ is a carboxy group or carboxylate anion or $R^3$ is a pharmaceutically acceptable salt-forming group or in-vivo hydrolysable ester group, wherein a compound of formula (I) as defined above in which $R^3$ is a carboxy protecting group has its group $CO_2R^3$ replaced by a group $CO_2R^3$ which is a carboxy group or a carboxylate anion, or in which $R^3$ is a pharmaceutically acceptable salt-forming group or in-vivo hydrolysable ester group.

The present invention further provides a process for the preparation of a compound of formula (I), which process comprises treating a compound of formula (II) or a salt thereof:

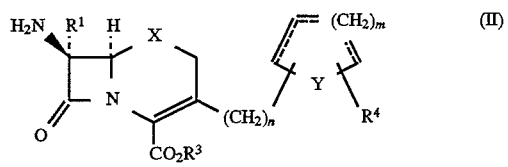

wherein $R^1$, $CO_2R^3$, $R^4$, m, n, X and Y are as hereinbefore defined, and wherein in the

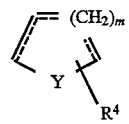

ring system the dotted line indicates that one pair of adjacent ring carbon atoms is joined by a C═C double bond, wherein any reactive groups may be protected, and wherein the amino group is optionally substituted with a group which permits acylation to take place; with an acid of formula (III) or a N-acylating derivative thereof:

$R^2OH$              (III)

wherein $R^2$ is the acyl group as defined with respect to formula (I) and wherein any reactive groups may be protected; and thereafter, if necessary or desired, carrying out one or more of the following steps:

i) removing any protecting groups;

ii) converting the group $CO_2R^3$ into a different group $CO_2R^3$;

iii) converting the group $R^2$ into a different group $R^2$;

iv) converting the group X and/or Y into a different group X and/or Y, for example S into SO or $SO_2$;

v) converting the product into a salt or ester.

Acids of formula (III) may be prepared by methods known in the art, or methods analogous to such processes. Suitable processes include those described, for example, in GB 2 107 307 B, GB 1,536,281, and GB 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —$P.R^7R^8$ wherein $R^7$ is an alkyl, haloalkyl, aryl, aralkyl, alkoxy, haloalkyl, aryl, aralkyl, alkoxy, haloalkoxy, aryloxy, aralkyloxy or dialkylamino group, $R^8$ is the same as $R^7$ or is halogen or $R^7$ and $R^8$ together form a ring; suitable such phosphorus groups being —$P(OC_2H_5)_2$, —$P(C_2H_5)_2$,

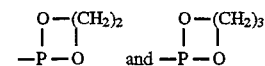

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl)acetamide, N,O-bis(trimethylsilyl)-trifluoroacetamide, N-methyl-N-trimethyl silylacetamide, N-methyl-N-trimethylsilyl-trifluoroacetamide, and N,N'-bis-(trimethylsilyl)urea, N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°–60° C., preferably 40°–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (e.g. chlorinating or brominating) agent such as phosphorus pentachloride, thionyl chloride, oxalyl chloride or phosgene.

Suitable mixed auhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimlde, for example, N,N'-diethyl-, dipropyl- or diisopropylcarbodiimide, N,N'-di-cyclohexyl-carbodiimide, or N-ethyl-N'-[3-(dimethylamino)propyl]-carbodiimide; a suitable carbonyl compound, for example, N,N'-carbonyldiimidazole or N,N'-carbonylditriazole; an isoxazolinium salt, for example, N-ethyl-5-phenyl isoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetontrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −400° to +30° C., if desired in the presence of an acid binding agent such as pyridine. A catalyst such as 4-dimethylaminopyridine may optionally also be added. A preferred solvent for the above acylation reaction is dichloromethane.

The optional removal of protecting group (i), the optional conversion of $CO_2R^3$ (ii), the optional conversion (iii) $R^2$ to a different $R^2$, $CO_2R^3$ to a different $CO_2R^3$ and (iv), X and/or Y to a different X and/or Y, and (v) the optional formation of a salt or ester, may be carried out using methods well known in the art of cephalosporin and penicillin chemistry.

For example, when the group X or Y is S, SO, or $SO_2$, the group X or Y may be converted into a different group Y by methods of oxidation or reduction well known in the art of cephalosporin and penicillin synthesis, as described, for example, in European Patent Application Publication No. 0 114 752. For example, sulphoxides fin which X or Y is SO) may be prepared from the corresponding sulphide (in which X or Y is S) by oxidation with a suitable oxidising agent, for example an organic peracid such as m-chloroperbenzoic acid.

A reduction step is generally effected by processes well known in the art of β-lactam chemistry, for example using phosphorus trichloride in dimethylformamide.

For example, removal of protecting groups may be carried out by any convenient method known in the art such that unwanted side reactions are miniraised. When for example $R^3$ is the protecting group p-methoxybenzyl, this group may suitably be removed by treatment of the protected compound with aluminium chloride in the presence of anisole. Separation of unwanted by-products may be carried out using standard methods.

In a further process of the invention, compounds of formula (II) may be prepared from known (e.g. V. Farina et al. J. Org. Chem., (1989) 54 4962; S. Torii et al. Tetrahedron Lett. (1982) 23 2187) compounds of formula (IV):

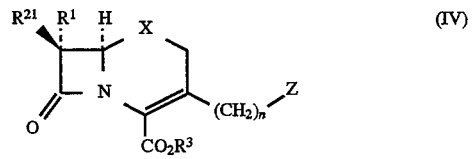

wherein $R^1$, $R^3$, X and n, are as defined in formula (I); $R^{21}$ is a group $R^2$ NH or a group which may be converted into or replaced by a group $R^2$ NH where $R^2$ is as defined in formula (I), and Z is a leaving group, with compounds of formula (V):

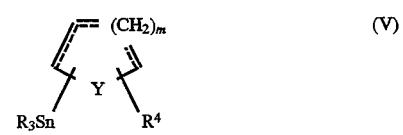

where $R^4$, Y and m are as defined in formula (I), the dotted line indicates that one pair of adjacent ring carbon atoms is joined by a C=C double bond, and R is an organic hydrocarbon group.

Suitably $R^{21}$ may be a substituted or protected amino group for example as defined above, in particular phenylaeetamido. Such amino substituting or protecting groups may be removed by known procedures to yield the amino group present in the compounds of formula (II) for example a phenylacetyl group may be removed from a phenylacetamido group by the known Delft cleavage reaction, e.g. by treatment with phosphorous pentachloride in the presence of N-methylmorpholine at reduced temperature.

Suitably when n is 0, Z may be a trifluoromethanesulphonyloxy group. Suitably when n is 1, Z may be a halogen, in particular chlorine. Suitably R in formula (V) may be an alkyl group, for example $C_{1-10}$ alkyl, such as n-butyl. The reaction between compounds of formula (IV) and (V) may suitably be carried out by a palladium mediated coupling, in the presence of a triorganophosphorous compound, in an organic solvent, for example under the conditions of the Stille reaction.

In a further process of the invention, compounds of formula (II) may be prepared by reaction of compounds of formula (IV) above in which X is $CH_2$ and Z is a trifluoromethanesulphonyloxy group, with a compound of formula (VI):

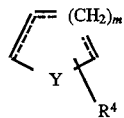

wherein $R_4$, Y and m are as defined in formula (I) and the dotted line indicates that one pair of adjacent ring carbon atoms are joined by a C=C double bond. This reaction too may for example suitably be carried out by a palladium mediated coupling.

In a further process of the invention, the unsaturated cyclic ether or thioether at the 3-position of the cephalosporin system in compounds of formula (I) or (II) above may be reduced to fore a compound as disclosed in WO 92/01696 e.g. of formula (I) on page 2 thereof, the content of which is included by reference, e.g. of formula (VII):

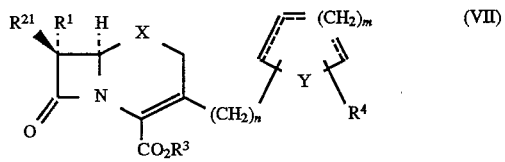

wherein $R^1$, $R^3$, $R^4$, X, Y, m and n are as defined in formula (I) above, and the cyclic ether or thio ether ring at the 3-position of the cephalosporin is saturated, and $R^{22}$ represents a group $R^2NH$ or $R^{21}$ as defined above or $H_2N$, and thereafter, if necessary or desired, carrying out one or more of the following steps:

i) removing any protecting groups;

ii) converting the group $CO_2R^3$ into a different group $CO_2R^3$;

iii) converting the group $R^2$ into a different group $R^2$;

iv) converting the group X and/or Y into a different group X and/or Y, for example S into SO or $SO_2$;

Suitably for example the reduction may be carried out by hydrogenation in the presence of Pd/C in an organic solvent.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives Such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (VIII) or a pharmaceutically acceptable salt or ester thereof:

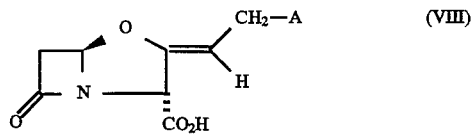

wherein

A is hydroxyl, substituted hydroxyl, thiol, substituted thiol, amino, mono- or di-hydrocarbyl- substituted amino, or mono- or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (IX) or a pharmaceutically acceptable salt or in vivo hydrolysable ester thereof:

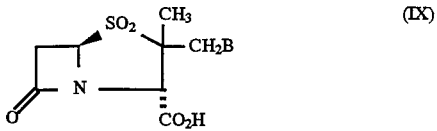

wherein

B represents hydrogen, halogen or a group of formula:

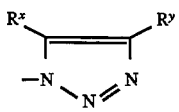

in which $R^x$ and $R^y$ are the same or different and each represents hydrogen, $(C_{1-6})$ alkoxycarbonyl or carboxy, or a pharmaceutically acceptable salt thereof.

Further suitable β-lactamase inhibitors include 6-alkylidene penems of formula (X):

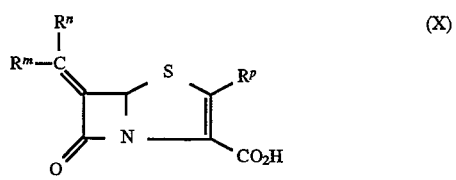

or a pharmaceutically acceptable salt or in vivo hydrolysable ester thereof, wherein $R^m$ and $R^n$ are the same or different and each represents hydrogen, or a $(C_{1-10})$ hydrocarbon or heterocyclic group optionally substituted with a functional group; and $R^p$ represents hydrogen or a group of formula $R^{13}$ or $-SR^{13}$ where $R^{13}$ is an optionally substituted $(C_{1-10})$ hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as E. coli and Gram-positive organisms such as S. aureus.

The following Examples illustrate the preparation of compounds of the invention and intermediates thereto, and the processes of the invention.

EXAMPLE 1

Diphenylmethyl (6R,7R)-3-(5,6-dihydro-4H-pyran-2-yl)-7-phenylacetamido-ceph-3-em-4-carboxylate a) Tri-n-butyl(5,6-dihydro-4H-pyran-2-yl)stannane Redistilled dihydropyran (1.0ml) in diethyl ether (10ml) containing THF (1 ml) was cooled to −70° C. in an argon atmosphere. t-Butyl lithium (10.72 ml of a 1.4M solution in pentane, 1.4 mol equiv.) was added dropwise, and the reaction mixture was then allowed to warm to −5° C. over 0.5 h. More THF (5 ml) was added to the turbid suspension, which was recooled to −70° C. Tri-n-butylchlorostannane (3.0 ml, 3.48 g, 1.03 mol equiv.) was added slowly (5 min) and the mixture warmed to 5° C. with stirring (3 h). Diethyl ether (30 ml) and water (10 ml) were added, and the organic layer was washed with water and dried (MgSO$_4$). Evaporation gave a liquid (3.4 g), which was chromatographed rapidly on basic alumina (grade 1) (15×5 cm) eluting with hexane, containing triethylamine (1%) (20 ml fractions). Fractions 4–15 afforded the title stannane[1–4] as a liquid (2.30 g, 56%); $v_{max}$ (CHCl$_3$) 0.75–1.03* (~15H, m), 1.23–1.38 (6H, m), 1.46–1.57 (6H, m), 1.80–1.88 (2H, m), 1.97–2.04 (2H, m), 3.90 (1H, dd, J 5.5, 4.5 Hz) and 4.72* (1H, t, J 3.5 Hz).

* Signals exhibited isotopic outriders.

1. D. MacLeod, D. Moorcroft, P. Quayle, M. R. J. Dorrity and J. F. Malone, Tetrahedron Lett., 1990, 31, 6077.
2. R. K. Boeckman and K. J. Bruza, Tetrahedron, 1981, 37, 3997.
3. S. Hanessian, M. Martin and R. C. Desai, J. Chem. Soc., Chem. Commun., 1986, 926.

b) Diphenylmethyl (6R,7R)-3-(5,6-dihydro-4H-pyran-2-yl)-7-phenylacetamidoceph-3-em-4-carboxylate Effected using the method of V. Farina, S. R. Baker and C. Sapino, Jr., Tetrahedron Lett., 1988, 29, 6043:—A solution of diphenylmethyl (6R,7R)-7-phenylacetamido-3-trifluoromethanesulphonyloxyceph-3-em-4-carboxylate (V. Farina, S. R. Barker and S. I. Hanck, *J. Org. Chem.*, 1989, 54, 4962) (0.316 g, 0.5 mmol) and tri-n-butyl(5,6-dihydro-4H-pyran-2-yl)-stannane (0.224 g, 0.6 mmol, 1.2 mol equiv.) in N-methylpyrrolidone was purged by bubbling with argon gas, and then zinc chloride (1.1 ml of a 1.0M solution in diethyl ether, 1.1 mmol, 2.2 mol equiv.), bis(dibenzylideneacetonyl)-palladium (0) (0.00575 g, 0.01 mmol, 2 mol %), and tri(2-furyl)phosphine (D. W. Allen, *J. Chem. Soc., Perkin Trans.*, 2, 1972, 63) (0.0046 g, 0.02 mmol, 4 mol %) were added. The mixture was stirred at room temperature in an argon atmosphere for 17 h. The solution was diluted with ethyl acetate (150 ml), washed twice with water and twice with brine and the organic layer dried and evaporated to give a residue (0.766 g). Rapid chromatography on silica gel (Merck 230–400 mesh ASTM, Art. 9385, 10×3 cm) followed by crystallisation from chloroform—hexane gave the title dienoate ester as an off-white solid (0.173 g, 61%); (Found: M$^+$, 566.1885. $C_{33}H_{30}N_2O_5S$ requires M, 566.1875); $\lambda_{max}$(EtOH) 299 nm; $\nu_{max}$(CHCl$_3$) 3270, 1780, 1730 and 1660 cm$^{-1}$; $\delta_H$(CDCl$_3$) 1.5–1.8 (2H, m), 1.83–2.00 (2H, m), 3.35–3.54 (2H, m), 3.39 and 3.53 (2H, ABq, J 18.5 Hz), 3.60 and 3.69 (2H, ABq, J 16 Hz), 4.76 (1H, t, J 4 Hz), 4.95 (1H, d, J 5 Hz), 5.84 (1H, dd, J 9, 5 Hz), 6.01 (1H, d, J 9 Hz), (1H, s) and 7.2–7.4 (15H, m); m/z (EI) 566 (M$^+$, 12%), 399 (20) and 167 (100).

EXAMPLE 2

Diphenylmethyl (6R,7R)-3-[(5,6-dihydro-4H-pyran-2-yl)methyl]-7-phenyl-acetamido-ceph-3-em-4-carboxylate Diphenylmethyl (6R,7R)-3-chloromethyl-7-phenylacetamido-ceph-3-em-4-carboxylate (S. Torii, H. Tanaka, N. Saitoh, T. Siroi, M. Sasaoka and J. Nokami, *Tetrahedron Lett.*, 1982, 23, 2187, and references cited therein) (1.065 g, 2 mmol), tri-n-butyl(5,6-dihydro-4H-pyran-2-yl)stannane (0.746 g), bis(dibenzylideneacetonyl) palladium (0) (0.023 g, 2 mol %) and tri(furan-2-yl) phosphine (0.019 g, 4 mol %) in THF (20 ml) were heated under reflux in an argon atmosphere for 3 h. The THF was evaporated and the residue chromatographed on silica gel (Art. 9385, 10×3 cm). Gradient elution [ethyl acetate—hexane (1:2 to 1:1)] gave the title cephem as a gum (1.15 g) which was crystalised from ethyl acetate—hexane as felted needles (1.02 g, 88%); m.p. 147°–149° C.; (Found: C, 69.95; H, 5.3; N, 4.9; S, 5.2. $C_{34}H_{32}N_2O_5S$ requires C,70.3; H, 5.55; N, 4.8; S, 5.5%); $\lambda_{max}$ (EtOH) 262 nm; $\nu_{max}$ (CHCl$_3$) 3420, 1780, 1725 and 1675 cm$^{-1}$; $\delta_H$ (250 MHz, CDCl$_3$) 1.73 (2H, m), 1.92 (2H, m), 3.10 and 3.23 (2H, ABq, J 15 Hz), 3.30 and 3.47 (2H, ABq, J 18 Hz), 3.62 and 3.69 (2H, ABq, J 16 Hz), 3.91 (2H, t, J 5 Hz), 4.95 (1H, t, J 3.5 Hz), 4.96 (1H, d, J 5 Hz), 5.79 (1H, dd, J 9, 5 Hz), 6.00 (1H, br d, J 9 Hz), 6.93 (1H, s) and 7.26–7.40 (15H, m); m/z (FAB, +ve ion, 3-nitrobenzyl alcohol, sodium acetate) 603 (MNa$^+$).

EXAMPLE 3

Diphenyhnethyl (6R,7R)-3-(4,5-dihydrofuran-2-yl)-7-phenylacetamido-ceph-3-em-4-carboxylate The title compound was prepared by the method described in example 1 using tri-n-butyl(4,5-dihydrofuran-2-yl)stannane in 49% yield; $\delta_H$(250 MHz, CDCl$_3$) 2.41 (2H, m), 3.44–3.66 (6H, m), 4.94 (1H, t, J 2.9 Hz), 4.97 (1H, d, J 5 Hz), 5.83 (1H, dd, J 9.1, 4.8 Hz), 6.02 (1H, d, J9.1 Hz), 7.04 (1H, s) and 7.24–7.37 (15H, m).

EXAMPLE 4

4-Methoxybenzyl (6R,7R)-3-(4,5-dihydrofuran-2-yl)-7-phenylacetamido-ceph-3-em-4-carboxylate 4-Methoxybenzyl (6R,7R)-7-phenylacetamido-3-trifluoromethane-sulphonyloxyceph-3-em-4-carboxylate (0.10 g), bis(dibenzylideneacetone)-palladium (0) (0.003 g) and tri-n-butyl(4,5-dihydrofuran-2-yl)stannane (0.122 g, 0.108 ml ) in dry N-methylpyrrolidinone (0.5 ml) were stirred together for 0.25 h. T.l.c. analysis (50% ethyl acetate—hexane) showed no starting material. The mixture was diluted with ethyl acetate, washed three times with water and with brine and then dried. The solution was concentrated to a small volume and then added dropwise to vigorously stirred hexane (50 ml). The suspension was centrifuged and the clear hexane decanted. The precipitate was washed with hexane and dried in vacuo, to give the title compound as a buff coloured, amorphous solid (0.08 g, 93%); $\delta_H$ (250 MHz, CDCl$_3$) 2.60 (2H, dt, J 9.8, 2.9 Hz), 3.38 and 3.47 (2H, ABq, J 18.1 Hz), 3.60 and 3.96 (2H, ABq, J 16.2 Hz), 3.80 (3H, s), 4.07 (1H, dt, J 18.6, 9.8 Hz), 4.21 (1H, dt, J 17.9, 8.5 Hz), 4.94 (1H, d, J 4.9 Hz), 5.02 (1H, t, 2.9 Hz), 5.17 and 5.23 (2H, ABq, J 12.0 Hz), 5.82 (1H, dd, J 9.1, 4.8 Hz), 6.01 (1H, d, J9.1 Hz), 6.88 (2H, d, J 8.7 Hz) and 7.25–7.41 (7H, m).

EXAMPLE 5

Sodium (6R,7S)-7-[2-(2-aminothiazol-4-yl)-2-(Z)-methoxylminoacetamido]-3-[(R and S)-2,5-dihydrofuran-2-yl]-1-carba-1-dethiaceph-3-em-4-carboxylate a) 4-Methoxybenzyl (6R,7S)-3-[(RS)-2,5-dihydrofuran-2-yl]-7-phenyl-acetamido- 1-carba-1-dethiaceph-3-em-4-carboxylate 4-Methoxybenzyl (6R,7S)-3-trifluoromethanesulphonyloxy-7-phenylacetamido-1-carba-1-dethiaceph-3-em-4-carboxylate (0.355 g) in benzene (8.9 ml) was treated with palladium acetate (7.1 mg), 1,1-bis(diphenylphosphino)ferrocene (35.5 mg), 2,3-dihydrofuran (0.236 ml) and diisopropylethylamine (0.108 ml) in a screw-top sealed vial at 70° C. for 35 minutes. The reaction mixture was concentrated to ca half volume and chromatographed on silica gel eluting with 20% ethyl acetate—dichloromethane. The title compound was obtained as a colourless gum (0.262 g, 86%); $\nu_{max}$(CH$_2$Cl$_2$) 3417, 1769, 1720, 1683, 1613 and 1516 cm$^{-1}$; $\delta_H$ (CDCl$_3$) 1.03–1.29 and 1.87–2.53 (4H, m), 3.60 (2H, s), 3.70–3.83 (5H, m and s), 4.66 (2H, m), 5.16–5.30 (3H, m), 5.52–5.55 and 5.60–5.72 (1H, m), 5.90 (1H, m), 5.97–6.01 and 6.07 (2H, m), 6.85–6.89 (2H, m) and 7.21–7.40 (7H, m); m/z (FAB, +ve ion, 3-nitrobenzyl alcohol, sodium acetate) 511 (MNa$^+$).

b) 4-Methoxybenzyl (6R,7S)-7-amino-3-[(R and S)-2,5-dihydrofuran-2-yl]-1-carba-1-dethiaceph-3-em-4-carboxylate 4-Methoxybenzyl (6R,7S)-3-[(RS)-2,5-dihydrofuran:2-yl]-7-phenylacetamido-1-carba-1-dethiaceph-3-em-4-carboxylate (0.256 g) in dichloromethane (2 ml), under argon was cooled to −20° C. and treated with N-methylmorpholine (0.106 g, 0.115 ml) followed by a solution of phosphorus pentachloride (0.164 g)in dichloromethane (4.1 ml) dropwise. The solution was stirred at −5° C. for 0.5 h then methanol (1 ml) added rapidly. After 0.5 h at room temperature water (1 ml) was added and the mixture stirred vigorously for 1 h. The dichloromethane was removed in vacuo and replaced with ethyl acetate. Concentrated aqueous ammonia was added to pH7 and the phases separated. The aqueous phase was extracted with ethyl acetate then the combined organic phases were washed with brine, dried, concentrated and chromatographed on silica gel eluting with ethyl acetate then 5% methanol in ethyl acetate to give the (S)-isomer of the title compound as a colourless foam (0.031 g, 16%); $v_{max}$ (CH$_2$Cl$_2$) 3403 (w), 1762, 1716, 1614 and 1516 cm$^{-1}$; $\delta_H$ (CDCl$_3$) 1.12–1.45 (1H, m), 2.04–2.09 (1H, m), 2.20–2.46 (2H, m), 3.67–3.75 (1H, m), 3.80 (3H, s), 4.47 (1H, d, J 5.4 Hz), 4.69–4.72 (2H, m), 5.19 (2H, s), 5.72–5.77 (1H, m), 5.96–6.01 (2H, m), 6.86–6.91 (2H, m) and 7.33–7.39 (2H, m); m/z (FAB, +ve ion, 3-nitrobenzyl alcohol, sodium acetate) 393 (MNa$^+$). Further elution provided the (R)-isomer of the title compound as a colourless foam (0.03 g, 16%); $v_{max}$ (CH$_2$Cl$_2$) 3402 (w), 1763, 1720, 1614 and 1516 cm$^{-1}$; $\delta_H$ (CDCl$_3$) 1.43–1.59 (1H, m), 1.94–2.09 (2H, m), 2.51–2.62 (1H, m), 3.64–3.76 (1H, m), 3.81 (3H, s), 4.44 (1H, d, J 5.5 Hz), 4.68–4.71 (2H, m), 5.23 (2H, s), 5.53–5.58 (1H, m), 5.98–6.06 (2H, m), 6.86–6.90 (2H, m) and 7.35–7.39 (2H, m); m/z (FAB, +ve ion, 3-nitrobenzyl alcohol, sodium acetate) 393 (MNa$^+$).

c) 4-Methoxybenzyl (6R,7S)-7-[2-(2-aminothiazol-4-yl)-2-(Z)-methoxyiminoacetamido]-3-[(S)-2,5-dihydrofuran-2-yl]-1-carba-1-dethiaceph-3-em-4-carboxylate 2-(2-Aminothiazol-4-yl)-2-(Z)-methoxylminoacetic acid (0.018 g) in dry DMF (0.5 ml) under argon, was cooled to –50° C. and treated with diisopropylethylamine (0.012 g, 0.016 ml) followed by methanesulphonyl chloride (0.01 g, 0.007 ml). The temperature was maintained between –45° C. and –40° C. for 0.5 h then a solution of 4-methoxybenzyl (6R,7S)-7-amino-3-[(S)-2,5-dihydrofuran-2-yl]-1-carba-1-dethiaceph-3-em-4-carboxylate (0.03 g) in DMF (0.5 ml) with pyridine (0.064 g, 0.065 ml) was added. The solution was warmed to room temperature over 2 h then diluted with ethyl acetate and washed with saturated sodium hydrogen carbonate, twice with water, then with brine and dried. The solvent was evaporated in vacuo and the residue chromatographed on silica gel eluting with ethyl acetate to give the title compound as a colourless foam, (0.031 g, 69%); $v_{max}$ (CH$_2$Cl$_2$) 3478, 3307, 3206, 1757, 1719, 1674, 1614, 1531 and 1516 cm$^{-1}$; $\delta_H$ (CDCl$_3$) 1.63 (1H, m), 2.08–2.47 (3H, m), 3.81 (3H, s), 3.87–3.93 (1H, m), 3.93 (3H, s), 4.70 (2H, m), 5.16 and 5.22 (2H, ABq, J 11.9 Hz), 5.65–4.75 (3H, m), 5.97–6.00 (2H, m), 6.67 (1H, s), 6.89 (2H, d, J 8.6 Hz), 7.34 (2H, d, J 8.6 Hz) and 8.47 (1H, d, J 7.8 Hz); m/z (FAB, +ve ion, 3-nitrobenzyl alcohol, sodium acetate) 554 (MH$^+$), 576 (MNa$^+$).

d) Sodium (6R,7S)-7-[2-(2-aminothiazol-4-yl )-2-(Z)-methoxyiminoacetamido]-3-[(S)-2,5-dihydrofuran-2-yl]-1-carba-1-dethiaceph-3-em-4-carboxylate A mixture of anisole (0.5 ml) and aluminium trichloride (0.022 g) in dichloromethane (0.5 ml) was stirred at –20° C. for 0.25 h and then cooled to –40° C. A solution of 4-methoxybenzyl (6R,7S)-7-[2-(2-aminothiazol-4-yl )-2-(Z)-methoxylminoacetamido]-3-[(S)-2,5-dihydrofuran-2-yl]-1-carba-1-dethiaceph-3-em-4-carboxylate (0.03 g) in dichloromethane (1 ml) was then added and the solution maintained at –40° C. for 10 min. 0.5M Trisodium citrate (2 ml) was added and the reaction mixture warmed to room temperature. After filtering the mixture through Kieselguhr the aqueous phase was separated and washed three times with dichloromethane (3 ml). The aqueous solution was chromatographed on HP20ss eluting with 0, 1 and 2% THF in water and the fractions containing the product, determined by EPLC, were combined, concentrated and freeze dried. The title compound was obtained as an amorphous colourless solid (0,015 g, 61%); $v_{max}$ (KBr) 1750, 1663, 1592 and 1532 cm$^{-1}$; $\delta_H$ [(CD$_3$)$_2$SO] 1.31–1.47 (1H, m), 1.75–2.15 (3H, m), 3.58–3.67 (1H, m), 3.82 (3H, s), 4.53 (2H, br s), 5.22 (1H, dd, J 8.7, 4.9 Hz), 5.70 (1H, dd, J 5.2, 2.8 Hz), 6.00 (2H, m), 6.74 (1H, s), 7.22 (2H, br s) and 9.17 (1H, d, J 8.7 Hz); m/z (FAB, +ve ion, glycerol) 456 (MH$^+$), 478 (MNa$^+$).

e) 4-Methoxybenzyl (6R,7S)-7-[2-(2-aminothiazol-4-yl)-2-(Z)-methoxylminoacetamido]-3-[(R)-2,5-dihydrofuran-2-yl]-1-carba-1-dethiaceph-3-em-4-carboxylate The procedure described in example 5c was repeated with 4-methoxybenzyl (6R,7S)-7-amino-3-[(R)-2,5-dihydrofuran-2-yl]-1-carba-1-dethiaceph-3-em-4-carboxylate (0.03 g) to provide the title compound as an amorphous colourless solid (0.030 g, 67%); $v_{max}$ (CH$_2$Cl$_2$) 1768, 1747, 1708, 1650 and 1608 cm$^{-1}$; $\delta_H$ (CDCl$_3$) 1.43–1.60 (1H, m), 1.86–2.09 (2H, m), 2.29–2.38 (1H, m), 3.76 (3H, s), 3.85 (4H, m and s), 4.52–4.68 (2H, m) 5.12 and 5.19 (2H, ABq, J 12.1 Hz), 5.46 (1tt, dd, J 8.9, 5.0 Hz), 5.68 (1H, m), 5.82 (1H, br s), 6.12 (1H, m), 6.86 (1H, s), 6.94 (2H, d, J 8.6 Hz), 7.23 (2H, br s), 7.36 (2H, d, J 8.6 Hz) and 9.29 (1H, d, J 8.9 Hz); m/z (FAB, +ve ion, thioglycerol) 554 (MH$^+$).

f) Sodium (6R,7S)-7-[2-(2-aminothiazol-4-yl)-2-(Z)-methoxyiminoacetamido]-3-[(R)-2,5-dihydrofuran-2-yl]-1-carba-1-dethiaceph-3-em-4-carboxylate The procedure described in example 5d was repeated with 4-methoxybenzyl (6R,7S)-7-[2-(2-aminothiazol-4-yl)-2-(Z)-methoxyiminoacetamido]-3-[(R)-2,5-dihydrofuran-2-yl]-1-carba-1-dethiaceph-3-em-4-carboxylate (0.026 g) with anisole (0.5 ml) and aluminium trichloride (0.019 g) to provide the title compound as an amorphous colourless solid (0.0114 g, 53%); $v_{max}$ (KBr) 1750, 1662, 1600 and 1532 cm$^{-1}$; $\delta_H$ [(CD$_3$)$_2$SO] 1.42–1.57 (1H, m), 1.72–1.86 (2H, m), 2.08–2.16 (1H, m), 3.56–3.63 (1H, m), 3.83 (3H, s), 4.46–4.62 (2H, m), 5.21 (1H, dd, J 8.7, 4.9 Hz), 5.57 (1H, m), 5.99 (1H, m), 6.22 (1H, m), 6.47 (1H, s), 7.23 (2H, br s) and 9.24 (1H, d, J 8.7 Hz); m/z (FAB, +ve ion, thioglycerol) 456 (MH$^+$), 478 (MNa$^+$)

EXAMPLE 6

4-Methoxybenzyl (6R,7S)-3-[(RS)-2,3-dihydrofuran-2-yl]-7-phenylacetamido-1-carba-1-dethiaceph-3-em-4-carboxylate The procedure described in example 5a was repeated using 4-methoxybenzyl (6R,7S)-3-trifluoromethanesulphonyloxy-7-phenyl-acetamido-1-carba-1-dethiaceph-3-em-4-carboxylate (0.05 g) with palladium acetate (0.0039 g, 25 mol %), 1,1-bis (diphenylphosphino)ferrocene (0.024 g, 50 mol 2,3-dihydrofuran (0.031 g, 0.033 ml) and diisopropylethylamine (0.011 g, 0.015 ml). After 3 h at 70° C. two products were observed by TLC analysis (20% ethyl acetate/dichloromethane). The two products were separated by chromatography on silica gel eluting with 20% ethyl acetate/dichloromethane. The more polar product was 4-methoxybenzyl (6R,7S)-3-[(RS)-2,5-dihydrofuran-2-yl]-7-phenyl-acetamido-1-carba-1-dethiaceph-3-em-4-carboxylate, identical with that described in Example 5a (0.0162 g, 38%). The less polar product was identified as the title compound, obtained as a yellowish solid (0.0127 g, 28%); as a 5:1 mixture of (R):(S) isomers; $\delta_H$ (CDCl$_3$) 1.14–1.33 (1H, m), 1.86–1.93 (1H, m), 2.05–2.43 (2H, m), 2.57–2.66 (1H, m), 2.70–2.82 (m, (R) isomer), 2.93–3.18 (m, (S) isomer), 3.60 (2H, s), 3.79 (4H, m and s), 4.86–4.91 (1H, m), 5.16 (s, (S) isomer), 5.18 (s, (R) isomer), 5.24 (1H, dd, J 6.7, 5.0 Hz), 5.68 (dd, J 11.0, 8.9 Hz, (S) isomer), 5.89

(dd,J 11.1, 8.4 Hz, (R) isomer), 6.06 (d, J 6.5 Hz, (S) isomer), 6.14 (d, J 6.6 Hz, (R) isomer), 6.27 (1H, m), 6.85–6.92 (3H, m) and 7.22–7.39 (7H, m).

EXAMPLE 7

4-Methoxybenzyl (6R,7S)-7-phenylacetamido-3-[(RS)-tetrahydrofuran-2-yl]-1-carba-1-dethiaceph-3-em-4-carboxylate 4-Methoxybenzyl (6R,7S)-3-[(RS)-2,3-dihydrofuran-2-yl]-7-phenylacetamido-1-carba-1-dethiaceph-3-em-4-carboxylate from example 6 (0.0122 g) and 10% palladium on carbon (0.003 g) in dry THF (1 ml) were hydrogenated for 0.5 h. TLC analysis (20% ethyl acetate/dichloromethane) showed complete conversion to a more polar material. The mixture was filtered through Kieselguhr and evaporated to provide the title compound as a colourless gum (0.0113 g, 90%). The $^1$H NMR spectrum showed a 5:1 mixture of (R):(S) isomers by comparison with an authentic sample (International Patent application, publication number WO92/01696).

EXAMPLE 8

4-Methoxybenzyl (6R,7S)-7-phenylacetamido-3-[(RS)-tetrahydrofuran-2-yl]-1-carba-1-dethiaceph-3-em-4-carboxylate 4-Methoxybenzyl (6R,7S)-3-[(RS)-2,5-dihydrofuran-2-yl]-7-phenylacetamido-1-carba-1-dethiaceph-3-em-4-carboxylate from example 5a (16.4mg) and 10% palladium on carbon (4 mg) in ethyl acetate (5 ml) were hydrogenated for 2 h. The mixture was filtered through celite and evaporated to provide the title compound as a colourless gum (16.1 mg, 93%). The $^1$H NMR spectrum showed a 1:1 mixture of (R):(S) isomers by comparison with example 7.

We claim:

1. A compound of formula (I) or a salt thereof:

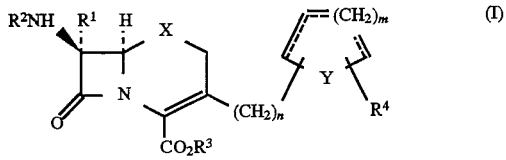

wherein:

$R^1$ is hydrogen, methoxy or formamido; $R^2$ is acyl groups of the formulae

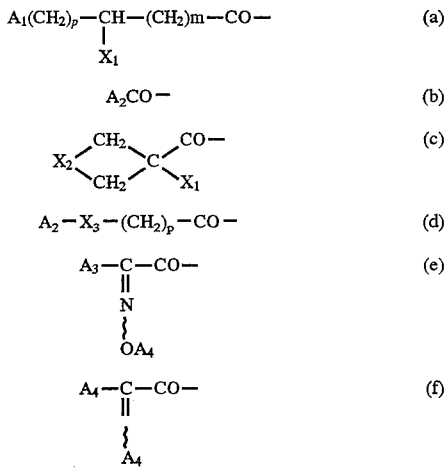

wherein p is 0, 1 or 2; m is 0, 1 or 2; $A_1$ is $(C_1-C_6)$alkyl, substituted $(C_{1-6})$alkyl wherein the substitutents may be as for $R^4$ above, $(C_{3-6})$cycloalkyl, cyclohexenyl, cyclohexadienyl, phenyl, thienyl, pyridyl, thiazolyl group, a $(C_{1-6})$akylthio group or $(C_{1-6})$alkyloxy; $X_1$ is a hydrogen or halogen atom, a carboxylic acid, carboxylic ester, sulphonic acid, azido, tetrazolyl, hydroxy, amino, ureido, or guanidino group; $A_2$ is phenyl, 2,6-dimethoxyphenyl, 2-alkoxy-1-naphthyl, 3-arylisoxazolyl, or 3-(2-chloro-6-fluorophenyl)-5-methylisoxazol-4-yl; $X_2$ is a —$CH_2OCH_2$—, —$CH_2SCH_2$— or alkylene group; $X_3$ is an oxygen or sulphur atom; $A_3$ is phenyl, naphthyl, furyl, aminothiazolyl or aminothiadiazolyl in which the amino group is optionally protected; and $A_4$ is hydrogen, $(C_{1-6})$alkyl, $(C_{3-8})$cycloalkyl, $(C_{3-8})$cycloalkyl$(C_{1-6})$alkyl, $(C_{1-6})$alkoxycarbonyl$(C_{1-6})$alkyl, $(C_{2-6})$alkenyl, carboxy$(C_{1-6})$alkyl, $(C_{2-6})$aklynyl, $(C_6-C_{10})$ aryl or $(C_{1-6})$alkyl substituted by up to three aryl groups; $CO_2R^3$ is a carboxy group or a carboxylate anion, or $R^3$ is a readily removable carboxy protecting group or a pharmaceutically acceptable salt-forming group or in vivo hydrolyzable ester group; $R^4$ represents hydrogen or up to four substituents, which may be present on any of the carbon atoms in the ring system shown, selected from $(C_1-C_6)$ alkyl, $(C_2-C_6)$alkenyl, $(C_2-C_6)$alkynyl, $(C_1-C_6)$alkoxy, hydroxy, halogen, amino, $(C_1-C_6)$alkylamino, acylamino wherein acyl is defined as above in formulae a–f, $((C_1-C_6)$ alkyl$)_2$-[dialkyl]amino, $CO_2R$, $OCOR$, $CONR_2$, $SO_2NR_2$ where R is hydrogen or $(C_1-C_6)$alkyl, $(C_6-C_{10})$aryl and $(C_2-C_9)$heterocyclyl, which may be the same or different and wherein any $R^4$ alkyl substituent is optionally substituted by one or more substituents selected from the list from which $R^4$ is selected; X is S, SO, or $SO_2$; Y is, S, SO or $SO_2$; n is 0 or 1; m is 1 or 2; and wherein in the ring system the dotted line indicates that one pair of adjacent ring carbon atoms is joined by a C=C double bond.

2. A compound of formula (I) as claimed in claim 1 wherein X is S, Y is S, $R^1$ is hydrogen, m is 1, n is 0 and the unsaturated cyclic ether or thioether is bonded to the cephalosporin nucleus at a ring carbon atom adjacent to the oxygen or sulphur heteroatom.

3. A compound of Formula (I) as claimed in claim 1 wherein the cyclic ether at the 3-position of the cephalosporin nucleus is a 4,5-dihydrofuran-2-yl, a 2,3-dihydrofuran-2-yl, a 2,5-dihydrofuran-2-yl or a 3,4-dihydro-2H-pyran-6-yl group.

4. A compound of formula (I) as claimed in claim 1, selected from:

(6R,7S)-7-[2-(2-aminothiazol-4-yl)-2-(Z)-methoxyiminoacetamido[-3-[(R and S)-2,5-dihydrofuran-2-yl]-1-carba-1-dethiaceph-3-em-4-carboxylic acid;

(6R,7S)-3-[(RS)-2,3-dihydrofuran-2-yl]-7-phenylacetamido-1-carba-1-dethiaceph-3-em-4-carboxylic acid; and (6R,7S)-3-[(RS)-2,3-dihydrofuran-2-yl]-7-phenylacetamido-1-carba-1-dethiaceph-3-em-4-carboxylic acid.

5. A method of treating bacterial infections in humans and animals which comprises the administration of a thereapeutically effective amount of an antibiotic compound of formula (I) as claimed in claim 1 or a pharmaceutically acceptable salt or in vivo hydrolysable ester thereof.

6. A pharmaceutical composition comprising a suitable pharmaceutical carrier and a compound of Formula I as described in claim 1 or a pharmaceutically acceptable salt or in vivo hydrolysable ester thereof.

* * * * *